US00RE39299E

(19) United States
(12) Reissued Patent
Vinik et al.

(10) Patent Number: US RE39,299 E
(45) Date of Reissued Patent: Sep. 19, 2006

(54) INGAP PROTEIN INVOLVED IN PANCREATIC ISLET NEOGENESIS

(75) Inventors: Aaron I. Vinik, Norfolk, VA (US); Gary L. Pittenger, Virginia Beach, VA (US); Ronit Rafaeloff-Phail, Indianapolis, IN (US); Lawrence Rosenberg, Montreal (CA); William P. Duguid, deceased, late of Montreal (CA); by Jean T. S. Duguid, legal representative, Quebec (CA)

(73) Assignees: Eastern Virginia Medical School of the Medical College of Hampton Roads, Norfolk, VA (US); McGill University, Quebec (CA)

(21) Appl. No.: 09/709,585

(22) Filed: Nov. 13, 2000

Related U.S. Patent Documents

Reissue of:
(64) Patent No.: 5,834,590
Issued: Nov. 10, 1998
Appl. No.: 08/401,530
Filed: Feb. 22, 1995

(51) Int. Cl.
*C07K 14/00* (2006.01)

(52) U.S. Cl. ..... 512/2; 530/350; 530/412; 435/69.1; 435/69.7; 514/12; 514/13; 514/14; 424/198.1

(58) Field of Classification Search ..... 530/350, 530/412; 574/2, 12–14; 435/69.1, 69.7; 424/198.1
See application file for complete search history.

(56) References Cited

U.S. PATENT DOCUMENTS 4,965,188 A * 10/1990 Mullis et al.
5,834,214 A 11/1998 Iovanna et al. ..... 435/2.9

FOREIGN PATENT DOCUMENTS

WO 94/15218 7/1994

OTHER PUBLICATIONS

Stein et al., "Antisense Oligonucleotides as Therapeutic Agents—Is the Bullet Really Magical?", *Science* 261:1004–1012 (1993).*
Bradley et al., "BoiTechnology, Modifying the Mouse", *Design and Desire* 10:534–539 (1992).*
Miller et al., "Human Gene Therapy Comes of Age", *Nature* 357:455–460 (1992).*
Watanabe et al., "Pancreatic Beta–Cell Replication and Amelioration of Surgical Diabetes by Reg Protein", *Proc. Natl. Acad. Sci. USA* 91:3589–3592 (1994).*
Liang et al., "Distribution and Cloning of Eukaryotic mRNAs by Means of Differential Display: Refinements and Optimization", *Nucleic Acids Research* 21(14):3269–3275 (1993).*
Rosenberg et al., "Reversal of Diabetes by the Induction of Islet Cell Neogenesis", *Transplantation Proceedings* 24(3):1027–1028 (1992).*
Rosenberg et al., (1992) Pancreatic Islet Cell Regeneration and Growth. Ed. Al Vinik, Plenum Press, New York, pp. 95–104.*
Pittenger GL. Et al. (1992) The Partial Isolation and Characterization of Ilotropin, a Novel Islet–Specific Growth Factor (abstract) Adv. Exp. Med. Biol. 321, pp. 123–132.*
Rouquier et al., "Rat Pancreatic Stone Protein Messenger RNA", *J. Biol. Chem.,* 266(2):786–791 (1991).*
Lasserre et al., "A Novel Gene (HIP) Activated in Human Primary Liver Cancer", *Cancer Research* 52:5089–5095 (1992).*
Terazono et al., "A Novel Gene Activated in Regenerating Islets", *J. Biol. Chem.,* 263(5):211–2114 (1988).*
Vinik et al., "Factors Controlling Pancreatic Islet Neogenesis", *Yale Journal of Biology and Medicine* 65:471–491 (1992).*
Orelle et al., "Human Pancreatitis–associated Protein" *J. Clin. Invest.* 90:2284–2291 (1992).*
International Search Report dated Jun. 23, 2000, Appl. No. EP 96905368, pp. 1–3.
Dusetti et al., Molecular Cloning, Genomic Organization, and Chromosomal Localization of the Human Pancreatitis–Associated Protein (PAP) Gene, Genomics, vol. 19, Jan. 1994, pp. 108–114.
Vinik, M.D. et al., "Factors Controlling Pancreatic Islet Neogenesis", The Yale Journal of Biology and Medicine, Inc., vol. 65, 1992, pp. 471–491.
Vinik, M.D. et al., "Factors Controlling Pancreatic Islet Neogenesis", Tumor Biology, vol. 14, 1993, pp. 184–200.

* cited by examiner

*Primary Examiner*—Karen Cochrane Carlson
(74) *Attorney, Agent, or Firm*—Banner & Witcoff LTD

(57) ABSTRACT

Cellophane wrapping (CW) of hamster pancreas induces proliferation of duct epithelial cells followed by endocrine cell differentiation and islet neogenesis. Using the mRNA differential display technique a cDNA clone expressed in cellophane wrapped but not in control pancreata was identified. Using this cDNA as a probe, a cDNA library was screened and a gene not previously described was identified and named INGAP.

32 Claims, 4 Drawing Sheets

FIG. 1A

```
CTGCAAGACA GGTACCATG ATG CTT CCC ATG ACC CTC TGT AGG ATG TCT TGG      52
                     Met Leu Pro Met Thr Leu Cys Arg Met Ser Trp
                      1               5                   10

ATG CTG CTT TCC TGC CTG ATG TTC CTT TCT TGG GTG GAA GGT GAA GAA      100
Met Leu Leu Ser Cys Leu Met Phe Leu Ser Trp Val Glu Gly Glu Glu
            15                  20                  25

TCT CAA AAG AAA CTG CCT TCT TCA CGT ATA ACC TGT CCT CAA GGC TCT      148
Ser Gln Lys Lys Leu Pro Ser Ser Arg Ile Thr Cys Pro Gln Gly Ser
        30                  35                  40

GTA GCC TAT GGG TCC TAT TGC TAT TCA CTG ATT TTG ATA CCA CAG ACC      196
Val Ala Tyr Gly Ser Tyr Cys Tyr Ser Leu Ile Leu Ile Pro Gln Thr
    45                  50                  55

TGG TCT AAT GCA GAA CTA TCC TGC CAG ATG CAT TTC TCA GGA CAC CTG      244
Trp Ser Asn Ala Glu Leu Ser Cys Gln Met His Phe Ser Gly His Leu
60                  65                  70                  75

GCA TTT CTT CTC AGT ACT GGT GAA ATT ACC TTC GTG TCC TCC CTT GTG      292
Ala Phe Leu Leu Ser Thr Gly Glu Ile Thr Phe Val Ser Ser Leu Val
                80                  85                  90

AAG AAC AGT TTG ACG GCC TAC CAG TAC ATC TGG ATT GGA CTC CAT GAT      340
Lys Asn Ser Leu Thr Ala Tyr Gln Tyr Ile Trp Ile Gly Leu His Asp
            95                  100                 105
```

FIG. 1B

```
CCC TCA CAT GGT ACA CTA CCC AAC GGA AGT GGA TGG AAG TGG AGC AGT      388
Pro Ser His Gly Thr Leu Pro Asn Gly Ser Gly Trp Lys Trp Ser Ser
        110                 115                 120

TCC AAT GTG CTG ACC TTC TAT AAC TGG GAG AGG AAC CCC TCT ATT GCT      436
Ser Asn Val Leu Thr Phe Tyr Asn Trp Glu Arg Asn Pro Ser Ile Ala
    125                 130                 135

GCT GAC CGT GGT TAT TGT GCA GTT TTG TCT CAG AAA TCA GGT TTT CAG      484
Ala Asp Arg Gly Tyr Cys Ala Val Leu Ser Gln Lys Ser Gly Phe Gln
140                 145                 150                 155

AAG TGG AGA GAT TTT AAT TGT GAA AAT GAG CTT CCC TAT ATC TGC AAA      532
Lys Trp Arg Asp Phe Asn Cys Glu Asn Glu Leu Pro Tyr Ile Cys Lys
                160                 165                 170

TTC AAG GTC TAGGGCAGTT CTAATTTCAA CAGCTTGAAA ATATTATGAA              581
Phe Lys Val

GCTCACATGG ACAAGGAAGC AAGTATGAGG ATTCACTCAG GAAGAGCAAG CTCTGCCTAC    641

ACACCCACAC CAATTCCCTT ATATCATCTC TGCTGTTTTT CTATCAGTAT ATTCTGTGGT    701

GGCTGTAACC TAAAGGCTCA GAGAACAAAA ATAAAATGTC ATCAAC                   747
```

FIG. 2

```
INGAP        MLPMTLC-RMSWMLLSCLMFLSWVEGEESQKKLPSS   35
PAP-I        MLHRLAFPVMSWMLLSCLMLLSQVQGEDSPKKIPSA   36
PAP-H/HIP    MLPPMALPSVSWMLLSCLMLLSQVQGEEPQRELPSA   36
PAP-III      MLPRVALTTMSWMLLSSLMLLSQVQGEDAKEDVPTS   36
PAP-II       MLPRLSFNNVSWTLLYYLFIF-QVRGEDSQKAVPST   35
REG/LITH     ----MT-RNKYFILLSCLMVLSPSQGQEAEEDLPSA   31
"DRICKAMER"

                *           *                 *
INGAP        RITCPQGSVAYGSYCYSLILIPQTWSNAELSCQMHF   71
PAP-I        RISCPKGSQAYGSYCYALFQIPQTWFDAELACQKRP   72
PAP-H/HIP    RIRCPKGSKAYGSHCYALFLSPKSWTDADLACQKRP   72
PAP-III      RISCPKGSRAYGSYCYALFSVSKSWFDADLACQKRP   72
PAP-II       RTSCPMGSKAYRSYCYTLVTTLKSWFQADLACQKRP   71
REG/LITH     RITCPEGSNAYSSYCYYFMEDHLSWAEADLFCQNMN   67
"DRICKAMER"        G                         C

INGAP        SGHLAFLLSTGEITFVSSLVKNSLTAYQYIWIGLHD   107
PAP-I        EGHLVSVLNVAEASFLASMVKNTGNSYQYIWIGLHD   108
PAP-H/HIP    SGNLVSVLSGAEGSFVSSLVKSIGNSYSYVWIGLHD   108
PAP-III      SGHLVSVLSGSEASFVSSLIKSSGNSGQNVWIGLHD   108
PAP-II       SGHLVSILSGGEASFVSSLVTGRVNNNQDIWIWLHD   107
REG/LITH     SGYLVSVLSQAEGNFLASLIKESGTTAANVWIGLHD   103
"DRICKAMER"                                   G TD

INGAP        PSHGTLPNGSGWKWSSSNVLTFYNWERNPSIAADRG   143
PAP-I        PTLGGEPNGGGWEWSNNDIMNYVNWERNPSTALDRG   144
PAP-H/HIP    PTQGTEPNGEGWEWSSSDVMNYFAWERNPSTISSPG   144
PAP-III      PTLGQEPNRGGWEWSNADVMNYFNWETNPSSVSGS-   143
PAP-II       PTMGQQPNGGGWEWSNSDVLNYLNWDGDPSSTVNRG   143
REG/LITH     P-----KNNRRWHWSSGSLFLYKSWDTGYPNNSNRG   134
"DRICKAMER"                  T         W    P     G
              *                  *        *
INGAP        YCAVLSQKSGFQKWRDFNCENELPYICKFKV   175
PAP-I        FCGSLSRSSGFLRWRDTTCEVKLPYVCKFTG   176
PAP-H/HIP    HCASLSRSTAFLRWKDYNCNVRLPYVCKFTD   176
PAP-III      HCGTLTRASGFLRWRENNCISELPYVCKFKA   175
PAP-II       NCGSLTATSEFLKWGDHHCDVELPFVCKFKQ   175
REG/LITH     YCVSVTSNSGYKKWRDNSCDAQLSFVCKFKA   165
"DRICKAMER"  EC        G    WND  C        CE
```

INGAP PROTEIN INVOLVED IN PANCREATIC ISLET NEOGENESIS

Matter enclosed in heavy brackets [ ] appears in the original patent but forms no part of this reissue specification; matter printed in italics indicates the additions made by reissue.

*This application is a reissue application of U.S. Pat. No. 5,834,590, filed as application Ser. No. 08/401,530 on Feb. 22, 1995.*

BACKGROUND OF THE INVENTION

Pancreatic islets of Langerhans are the only organ of insulin production in the body. However, they have a limited capacity for regeneration. This limited regeneration capacity predisposes mammals to develop diabetes mellitus. Thus there is a need in the art of endocrinology for products which can stimulate the regeneration of islets of Langerhans to prevent or ameliorate the symptoms of diabetes mellitus.

One model of pancreatic islet cell regeneration involves cellophane-wrapping of the pancreas in the Syrian golden hamster (1). Wrapping of the pancreas induces the formation of new endocrine cells which appear to arise from duct epithelium (2–4). There is a need in the art to identify and isolate the factor(s) which is responsible for islet cell regeneration.

SUMMARY OF THE INVENTION

It is an object of the invention to provide a preparation of a mammalian protein or polypeptide portions thereof involved in islet cell neogenesis.

It is another object of the invention to provide a DNA molecule encoding a mammalian protein involved in islet cell neogenesis.

It is yet another object of the invention to provide a preparation of a mammalian INGAP (islet neogenesis associated protein) protein.

It is still another object of the invention to provide nucleotide probes for detecting mammalian genes involved in islet cell neogenesis, It is an object of the invention to provide a method for isolation of INGAP genes from a mammal.

It is another object of the invention to provide an antibody preparation which is specifically immunoreactive with an INGAP protein.

It is yet another object of the invention to provide methods of producing INGAP proteins.

It is an object of the invention to provide methods for treating diabetic mammals.

It is another object of the invention to provide methods for growing pancreatic islet cells in culture.

It is still another object of the invention to provide methods of enhancing the life span of pancreatic islet cells encapsulated in polycarbon shells.

It is an object of the invention to provide methods of enhancing the number of pancreatic islet cells in a mammal.

It is an object of the invention to provide transgenic mammals.

It is another object of the invention to provide genetically engineered mammals.

It is yet another object of the invention to provide methods of identifying individual mammals at risk for diabetes.

It is an object of the invention to provide methods of detecting INGAP protein in a sample from a mammal.

It is still another object of the invention to provide a method of treating isolated islet cells to avoid apoptosis.

It is another object of the invention to provide methods of treating mammals receiving islet cell transplants.

It is an object of the invention to provide a method of inducing differentiation of β cell progenitors.

It is an object of the invention to provide a method of identifying β cell progenitors.

It is another object of the invention to provide a method of treating a mammal with pancreatic endocrine failure.

It is an object of the invention to provide antisense constructs for regulating the expression of INGAP.

It is yet another object of the invention to provide a method for treating nesidioblastosis.

It is still another object of the invention to provide kits for detecting mammalian INGAP proteins.

It is an object of the invention to provide pharmaceutical compositions for treatment of pancreatic insufficiency.

These and other objects of the invention are provided by one or more of the embodiments described below.

In one embodiment a preparation of a mammalian INGAP protein is provided. The preparation is substantially free of other mammalian proteins.

In another embodiment an isolated cDNA molecule is provided. The cDNA molecule encodes a mammalian INGAP protein.

In still another embodiment of the invention a preparation of a mammalian INGAP protein is provided. The preparation is made by the process of:

inducing mammalian pancreatic cells to express INGAP protein by cellophane-wrapping; and purifying said INGAP protein from said induced mammalian pancreatic cells.

In yet another embodiment of the invention a nucleotide probe is provided. The probe comprises at least 20 contiguous nucleotides of the sequence shown in SEQ ID NO: 1.

In another embodiment of the invention a preparation of INGAP protein of a mammal is provided. The preparation is substantially purified from other proteins of the mammal. The INGAP protein is inducible upon cellophane-wrapping of pancreas of the mammal.

In yet another embodiment of the invention a method of isolating an INGAP gene from a mammal is provided. The method comprises:

hybridizing one or more oligonucleotides comprising at least 10 contiguous nucleotides of the sequence shown in SEQ ID NO: 1 to genomic DNA or cDNA of said mammal;

identifying DNA molecules from said genomic DNA or cDNA which hybridize to said one or more oligonucleotides.

In still another embodiment of the invention an isolated cDNA molecule is provided. The cDNA molecule is obtained by the process of:

hybridizing one or more oligonucleotides comprising at least 10 contiguous nucleotides of the sequence shown in SEQ ID NO: 1 to genomic DNA or cDNA of said mammal;

identifying DNA molecules from said genomic DNA or cDNA which hybridize to said one or more oligonucleotides.

In another embodiment of the invention an antibody is provided. The antibody is specifically immunoreactive with a mammalian INGAP protein.

According to still another embodiment of the invention a method of producing a mammalian INGAP protein is provided. The method comprises the steps of:

providing a host cell transformed with a cDNA encoding a mammalian INGAP protein;

culturing the host cell in a nutrient medium so that the INGAP protein is expressed; and harvesting the INGAP protein from the host cell or the nutrient medium.

According to yet another embodiment of the invention a method of producing a mammalian INGAP protein is provided. The method comprises the steps of: providing a host cell comprising a DNA molecule obtained by the process of:

hybridizing one or more oligonucleotides comprising at least 10 contiguous nucleotides of the sequence shown in SEQ ID NO: 1 to genomic DNA or cDNA of said mammal;

identifying DNA molecules from said genomic DNA or cDNA which hybridize to said one or more oligonucleotides;

culturing the host cell in a nutrient medium so that the mammalian INGAP protein is expressed; and harvesting the mammalian INGAP protein from the host cells or the nutrient medium.

According to another embodiment of the invention a method of treating diabetic mammals is provided. The method comprises:

administering to a diabetic mammal a therapeutically effective amount of an INGAP protein to stimulate growth of islet cells.

According to another embodiment of the invention a method of growing pancreatic islet cells in culture is provided. The method comprises:

supplying an INGAP protein to a culture medium for growing pancreatic islet cells; and growing islet cells in said culture medium comprising INGAP protein.

According to another embodiment of the invention a method of enhancing the life span of pancreatic islet cells encapsulated in a polycarbon shell is provided. The method comprises:

adding to encapsulated pancreatic islet cells an INGAP protein in an amount sufficient to enhance the survival rate or survival time of said pancreatic islet cells.

According to another embodiment of the invention a method of enhancing the number of pancreatic islet cells in a mammal is provided. The method comprises:

administering a DNA molecule which encodes an INGAP protein to a pancreas in a mammal.

According to another embodiment of the invention a method of enhancing the number of pancreatic islet cells in a mammal is provided. The method comprises:

administering an INGAP protein to a pancreas in a mammal.

According to another embodiment of the invention a transgenic mammal is provided. The mammal comprises an INGAP gene of a second mammal.

According to another embodiment of the invention a non-human mammal is provided. The mammal has been genetically engineered to contain an insertion or deletion mutation of an INGAP gene of said mammal.

According to another embodiment of the invention a method of identifying individual mammals at risk for diabetes is provided. The method comprises:

identifying a mutation in an INGAP gone of a sample of an individual mammal, said mutation causing a structural abnormality in an INGAP protein encoded by said gene or causing a regulatory defect leading to diminished or obliterated expression of said INGAP gene.

According to another embodiment of the invention a method of detecting INGAP protein in a sample from a mammal is provided. The method comprises:

contacting said sample with an antibody preparation which is specifically immunoreactive with a mammalian INGAP protein.

According to another embodiment of the invention a method of treating isolated islet cells of a mammal to avoid apoptosis of said cells is provided. The method comprises:

contacting isolated islet cells of a mammal with a preparation of a mammalian INGAP protein, substantially purified from other mammalian proteins, in an amount sufficient to increase the survival rate of said isolated islet cells.

According to another embodiment of the invention a method of treating a mammal receiving a transplant of islet cells is provided. The method comprises:

administering a preparation of a mammalian INGAP protein to a mammal receiving a transplant of islet cells, wherein said step of administering is performed before, during, or after said transplant.

According to another embodiment of the invention a method of inducing differentiation of β cell progenitors is provided. The method comprises:

contacting a culture of pancreatic duct cells comprising β cell progenitors with a preparation of a mammalian INGAP protein substantially free of other mammalian proteins, to induce differentiation of said β cell progenitors.

In yet another embodiment of the invention a method is provided for identification of β cell progenitors. The method comprises:

contacting a population of pancreatic duct cells with a mammalian INGAP protein; and detecting cells among said population to which said INGAP protein specifically binds.

According to another embodiment of the invention a method of treating a mammal with pancreatic endocrine failure is provided. The method comprises:

contacting a preparation of pancreatic duct cells comprising β cell progenitors isolated from a mammal afflicted with pancreatic endocrine failure with a preparation of a mammalian INGAP protein substantially free of other mammalian proteins to induce differentiation of said β cell progenitors; and autologously transplanting said treated pancreatic duct cells into said mammal.

According to another embodiment of the invention an antisense construct of a mammalian INGAP gene is provided. The construct comprises:

a promoter, a terminator, and a nucleotide sequence consisting of a mammalian INGAP gene, said nucleotide sequence being between said promoter and said terminator, said nucleotide sequence being inverted with respect to said promoter, whereby upon expression from said promoter an mRNA complementary to native mammalian INGAP mRNA is produced.

According to another embodiment of the invention a method of treating nesidioblastosis is provided. The method comprises:

administering to a mammal with nesidioblastosis an antisense construct as described above, whereby overgrowth of β cells of said mammal is inhibited.

According to another embodiment of the invention a kit for detecting a mammalian INGAP protein in a sample from a mammal is provided. The kit comprises:

an antibody preparation which is specifically immunoreactive with a mammalian INGAP protein; and a polypeptide which comprises a sequence of at least 15 consecutive amino acids of a mammalian INGAP protein.

According to another embodiment of the invention a pharmaceutical composition for treatment of pancreatic insufficiency is provided. The composition comprises:

a mammalian INGAP protein in a pharmaceutically acceptable diluent or carrier.

According to another embodiment of the invention a pharmaceutical composition is provided. The composition comprises:

a preparation of a polypeptide which comprises a sequence of at least 15 consecutive amino acids of a mammalian INGAP protein and a pharmaceutically acceptable diluent or carrier.

These and other embodiments of the invention provide the art with means of stimulating and inhibiting islet cell neogenesis Means of diagnosis of subsets of diabetes mellitus are also provided by this invention.

BRIEF DESCRIPTION OF THE DRAWINGS

FIG. 1A and 1B Nucleotide sequence of hamster INGAP SEQ ID NO:1 and deduced sequence of encoded immature protein SEQ ID NO:2. The non-coding sequences are in lower case letters, and the polyadenylation signal is underlined.

FIG. 2. Comparison of amino acid sequences of INGAP SEQ ID NO:2, rat PAP-I (PAP-I) (18) SEQ ID NO: 3, Human PAP/HIP (PAP-H/HIP)(10, 11) SEQ ID NO:4, rat PAP-Ill (PAP III)(9) SEQ ID NO: 5, rat PAP-II (PAP-R)(8) SEQ ID NO:6, Rat Reg/PSP/Lithostatine (REG/LITH)(13, 15) SEQ ID NO: 7 and the invariable motif found by Drickamer in cell members of C-type lectins (Drickamer) (12). Six conserved cysteines are marked by asterisks and the 2 putative N-glycosylation sites of INGAP are underlined and in bold letters.

DETAILED DESCRIPTION OF THE PREFERRED EMBODIMENTS

Figures 3A, 3B, 3C:
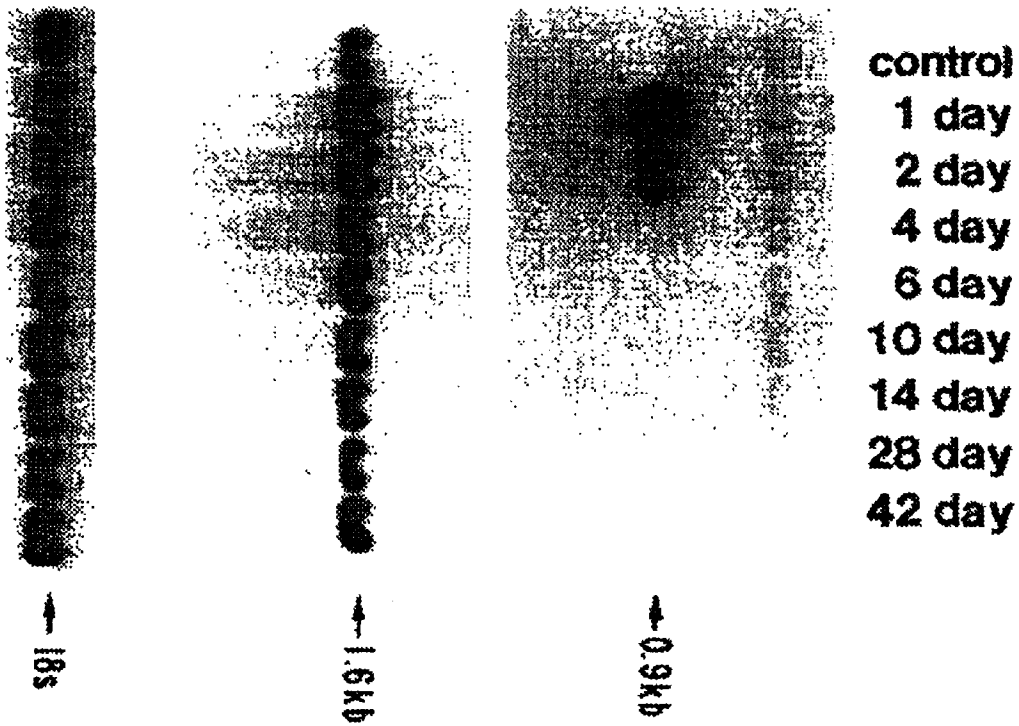
FIGS. 3A and 3C. Northern blot analysis of INGAP and amylase gene expression in pancreatic tissue from control and wrapped hamster pancreas. 30 g of heat denatured total RNA was separated by electrophoresis on a 1.2% agarose, 0.6% formaldehyde/MOPS denaturing gel, and transferred to nylon membrane. Membranes were hybridized with a 747 bp hamster INGAP cDNA probe (cloned in our lab) (A), a 1000 bp rat amylase cDNA probe (generously giver by Chris Newgard Dallas, Texas) (13) and with an 18S ribosomal 24mer synthetic oligonucleotide probe to control for RNA integrity and loading (C).

We now report the identification of a gene, INGAP, that shows staining homology to the pancreatitis associated protein (PAP) family of genes (7–11). The predicted protein shares the carbohydrate recognition domain (CRD) of the calcium dependent C-type lectins as defined by Drickamer (12). INGAP protein plays a role in stimulation of islet neogenesis, in particular, in beta cell regeneration from ductal cells.

The cDNA sequence of a mammalian INGAP is provided in SEQ ID NO: 1. The predicted amino acid sequence is shown in SEQ ID NO:2. These sequences were determined from nucleic acids isolated from hamster, but it is believed that other mammalian species will contain INGAP genes which are quite similar. For example, one would expect homologous genes to contain at least about 70% identity. Closer species would be expected to have at least about 75%, 80%, or even 85% identity. In contrast, other family members of the calcium dependent C-type lectins contain at most 60% identity with INGAP.

The DNA sequence provided herein can be used to form vectors which will replicate the gene in a host cell, and may also express INGAP protein. DNA sequences which encode the same amino acid sequence as shown in SEQ ID NO:2 can also be used, without departing from the contemplation of the invention. DNA sequences coding for other mammalian INGAPs are also within the contemplation of the invention. Suitable vectors, for both prokaryotic and eukaryotic cells, are known in the art. Some vectors are specifically designed to effect expression of inserted DNA segments downstream from a transcriptional and translational control site. One such vector for expression in eukaryotic cells employs EBNA His, a plasmid which is available commercially from InVitrogen Corp. The loaded vector produces a fusion protein comprising a portion of a histidine biosynthetic enzyme and INGAP Mother vector, which is suitable for use in prokaryotic cells, is pCDNA3. Selection of a vector for a particular purpose may be made using knowledge of the properties and features of the vectors, such as useful expression control sequences. Vectors may be used to transform or transfect host cells, either stably or transiently. Methods of transformation and transfection are known in the art, and may be used according to suitability for a particular host cell. Host cells may be selected according to the purpose of the transfection. A suitable prokaryotic host is E. coli DH5a. A suitable eukaryotic host is cos7, an African Green Monkey kidney cell line. For some purposes, proper glycosylation of INGAP may be desired, in which case, a suitable host cell should be used which recognizes the glycosylation signal of INGAP Probes comprising at least 10, 15, 20, or 30 nucleotides of contiguous sequence according to SEQ ID NO: 1 can be used for identifying INGAP genes in particular individuals or in members of other species. Appropriate conditions for hybridizations to same or different species' DNA an known in the art as high stringency and low stringency, respectively. These can be used in a variety of formats according to the desired use. For example, Southern blots, Northern blots, and in situ colony hybridization, can be used as these are known in the art. Probes typically an DNA or RNA oligomers of at least 10, 15, 20, or 30 nucleotides. The probe may be labeled with any detectable moiety known in the art, including radiolabels, fluorescent labels, enzymes, etc. Probes may also be derived from other mammalian INGAP gene sequences.

INGAP genes can be isolated from other mammals by utilizing the nucleotide sequence information provided herein. (More laboriously, they can be isolated using the same method described in detail below for isolation of the hamster INGAP gene.) Oligonucleotides comprising at least 10 contiguous nucleotides of the disclosed nucleotide sequence of INGAP are hybridized to genomic DNA or cDNA of the mammal. The DNA may conveniently be in the form of a library of clones. The oligonucleotides may be labelled with any convenient label, such as a radiolabel or an enzymatic or fluorescence label. DNA molecules which hybridize to the probe one isolated. Complete genes can be constructed by isolating overlapping DNA segments, for example using the first isolated DNA as a probe to contiguous DNA in the library or preparation of the mammal's DNA. Confirmation of the identity of the isolated DNA can be made by observation of the pattern of expression of the gene in the pancreas when subjected to cellophane wrapping, for example. Similarly, the biological effect of the encoded product upon pancreatic ductal cells will also serve to identify the gene as an INGAP gene.

If two oligonucleotides are hybridized to the genomic DNA or cDNA of the mammal then they can be used a primers for DNA synthesis, for example using the polymerase chain reaction or the ligase chain reaction. Construction of a full-length gene and confirmation of the identity of the isolated gene can be performed as described above.

INGAP protein may be isolated according to the invention by inducing mammalian pancreatic cells to express INGAP protein by means of cellophane-wrapping. This technique is described in detail in reference no. 1 which is expressly incorporated herein. Briefly, the pancreas is exposed and a strip of sterile cellophane tape is wrapped carefully around the head of the gland, so as not to crush the underlying tissue. Duct ligation is not involved. INGAP protein so produced may be purified from other mammalian proteins by means of immunoaffinity techniques, for example, or other techniques known in the art of protein purification. An antibody specific for a mammalian INGAP is produced using all, or fragments of, the amino acid sequence of an INGAP protein, such as shown in SEQ ID NO: 2, as immunogens. The immunogens can be used to identify and purify immunoreactive antibodies. Monoclonal or polyclonal antibodies can be made as is well known in the art. The antibodies can be conjugated to other moieties, such as detectable labels or solid support materials. Such antibodies can be used to purify proteins isolated from mammalian pancreatic cells or from recombinant cells. Hybridomas which secrete specific antibodies for an INGAP protein are also within the contemplation of the invention.

Host cells as described above can be used to produce a mammalian INGAP protein. The host cells comprise a DNA molecule encoding a mammalian INGAP protein. The DNA can be according to SEQ ID NO:1, or isolated from other mammals according to methods described above. Host cells can be cultured in a nutrient medium under conditions where INGAP protein is expressed. INGAP protein can be isolated from the host cells or the nutrient medium, if the INGAP protein is secreted from the host cells.

It has now been found that INGAP and fragments thereof are capable of inducing and stimulating islet cells to grow. Moreover, they are capable of inducing differentiation of pancreatic duct cells, and of allowing such cells to avoid the apoptotic pathway. Thus many therapeutic modalities are now possible using INGAP fragments thereof, and nucleotide sequences encoding INGAP Therapeutically effective amounts of INGAP are supplied to patient pancreata, to isolated islet cells, and to encapsulated pancreatic islet cells, such as in a polycarbon shell. Suitable amounts of INGAP for therapeutic purposes range from 1–150 μg/kg of body weight or in vitro from 1–10,000 μg/ml. Optimization of such dosages can be ascertained by routine testing. Methods of administering INGAP to mammals can be any that are known in the art, including subcutaneous, via the portal vein, by local perfusion, etc.

Conditions which can be treated according to the invention by supplying INGAP include diabetes mellitus, both insulin dependent and non-insulin dependent, pancreatic insufficiency, pancreatic failure, etc. Inhibition of INGAP expression can be used to treat nesidioblastosis.

According to the present invention, it has now been found that a small portion of INGAP is sufficient to confer biological activity. A fragment of 20 amino acids of the sequence of SEQ ID NO: 2, from amino acid #103–#122 is sufficient to stimulate pancreatic ductal cells to grow and proliferate. The effect has been seen on a rat tumor duct cell line, a hamster dad cell line, a hamster insulinoma cell line, and a rat insulinoma cell line. The analogous portions of other mammalian INGAP proteins are quite likely to have the same activity. This portion of the protein is not similar to other members of the pancreatitis associated protein (PAP) family of proteins. It contains a glycosylation site and it is likely to be a primary antigenic site of the protein as well. This fragment has been used to immunize mice to generate monoclonal antibodies.

The physiological site of expression of INGAP has been determined INGAP is expressed in acinar tissue, in the exocrine portion of the pancreas. It is not expressed in ductal or islet cells, i. e., the paracrine portion of the pancreas. Expression occurs within 24–48 hours of induction by means of cellophane wrapping.

Transgenic animals according to the present invention are mammals which carry an INGAP gene from a different mammal. The transgene can be expressed to a higher level than the endogenous INGAP genes by judicious choice of transcription regulatory regions. Methods for making transgenic animals are well-known in the art, and any such method can be used. Animals which have been genetically engineered to carry insertions, deletions, or other mutations which alter the structure of the INGAP protein or regulation of expression of INGAP are also contemplated by this invention. The techniques for effecting these mutations are known in the art.

Diagnostic assays are also contemplated within the scope of the present invention. Mutations in INGAP can be ascertained in samples such as blood, amniotic fluid, chorionic villus, blastocyst, and pancreatic cells. Such mutations identify individuals who are at risk for diabetes. Mutations can be identified by comparing the nucleotide sequence to a wild-type sequence of an INGAP gene. This can be accomplished by any technique known in the art, including comparing restriction fragment length polymorphisms, comparing polymerise chain reaction products, nuclease protection assays, etc. Alternatively, altered proteins can be identified, e.g., immunologically or biologically.

The present invention also contemplates the use of INGAP antisense constructs for treating nesidioblastosis, a condition characterized by overgrowth of β cells. The antisense construct is administered to a mammal having nesidioblastosis, thereby inhibiting the overgrowth of β cells. An antisense construct typically comprises a promoter, a terminator, and a nucleotide sequence consisting of a mammalian INGAP gene. The INGAP sequence is between the promoter and the terminator and is inverted with respect to the promoter as it is expressed naturally. Upon expression from the promoter, an mRNA complementary to native mammalian INGAP is produced.

Immunological methods for assaying INGAP in a sample from a mammal are useful, for example, to monitor the therapeutic administration of INGAP. Typically an antibody specific for INGAP will be contacted with the sample and the binding between the antibody and any INGAP in the sample will be detected This can be by means of a competitive binding assay, in which the incubation mixture is spiked with a known amount of a standard INGAP preparation, which may conveniently be detectably labeled. Alternatively, a polypeptide fragment of INGAP may be used as a competitor. In one particular assay format, the antibodies are bound to a solid phase or support, such as a bead, polymer matrix, or a microtiter plate.

According to the present invention, pancreatic duct cells of a mammal with pancreatic endocrine failure an be removed from the body and treated in vitro. The duct cells typically comprise β cell progenitors. Thus treatment with a preparation of a mammalian INGAP protein will induce differentiation of the β cell progenitors. The duct cells are contacted with a preparation of a mammalian INGAP protein substantially free of other mammalian proteins. The treated cells can then used as an autologous transplant into the mammal from whom they were derived. Such an autologous treatment minimizes adverse host versus graft reactions involved in transplants.

INGAP protein can also be used to identify those cells which bear receptors for INGAP. Such cells are likely to be the β cell progenitors, which are sensitive to the biological effects of INGAP. INGAP protein can be detestably labeled, such as with a radiolabel or a fluorescent label, and then contacted with a population of cells from the pancreatic duct. Cells which bind to the labeled protein will be identified as those which bear receptors for INGAP, and thus are β cell progenitors. Fragments of INGAP can also be used for this purpose, as can immobilized INGAP which can be used to separate cells from a mixed population of cells to a solid support. INGAP can be immobilized to solid phase or support by adsorption to a surface, by means of an antibody, or by conjugation. Any other means as is known in the art can also be used.

Kits are provided by the present invention for detecting a mammalian INGAP protein in a sample. This maybe useful, inter alia, for monitoring metabolism of INGAP during therapy which involves administration of INGAP to a mammal. The kit will typically contain an antibody preparation which is specifically immunoreactive with a mammalian INGAP protein. The antibodies may be polyclonal or monoclonal. If polyclonal they may be affinity purified to tender them monospecific. The kit will also typically contain a polypeptide which has at least 15 consecutive amino acids of a mammalian INGAP protein The polypeptide is used to compete with the INGAP protein in a sample for binding to the antibody. Desirably the polypeptide will be detectably labeled. The polypeptide will contain the portion of INGAP to which the antibody binds. Thus if the antibody is monoclonal, the polypeptide will successfully compete with INGAP by virtue of it containing the epitope of the antibody. It may also be desirable that the antibodies be bound to a solid phase or support, such as polymeric beads, sticks, plates, etc.

Pharmaceutical compositions containing a mammalian INGAP protein may be used for treatment of pancreatic insufficiency. The composition may alternatively contain a polypeptide which contains a sequence of at least 15 consecutive amino acids of a mammalian INGAP protein. The polypeptide will contain a portion of INGAP which is biologically active in the absence of the other portions of the protein. The polypeptide may be part of a larger protein, such as a genetic fusion with a second protein or polypeptide. Alternatively, the polypeptide may be conjugated to a second protein, for example, by means of a cross-linking agent. Suitable portions of INGAP proteins may be determined by homology with amino acids #103 to #122 of SEQ ID NO:2, or by the ability of test polypeptides to stimulate pancreatic duct cells to grow and proliferate. As is known in the art, it is often the case that a relatively small number of amino acids can be removed from either end of a protein without destroying activity. Thus it is contemplated within the scope of the invention that up to about 10% of the protein can be deleted, and still provide essentially all functions of INGAP Such proteins have at least about 130 amino acids, in the case of hamster INGAP.

The pharmaceutical composition will contain a pharmaceutically acceptable diluent or carrier. A liquid formulation is generally preferred. INGAP may be formulated at different concentrations or using different formulants. For example, these formulants may include oils, polymer; vitamins, carbohydrates, amino acids, salts, buffers, albumin, surfactants, or bulking agents. Preferably carbohydrates include sugar or sugar alcohols such as mono-, di-, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxethyl starch and carboxymethylcelloluose, or mixtures thereof. Sucrose is most preferred. Sugar alcohol is defined as a $C_4$ to $C_8$ hydrocarbon having an —OH group and includes galactitol, inositol, mannitol, xylitol, sorbitol, glycerol, and arabitol. Mannitol is most preferred. These sugars or sugar alcohols mentioned above may be used individually or in combination. There is no fixed limit to amount used as long as the sugar or sugar alcohol is soluble in the aqueous preparation. Preferably, the sugar or sugar alcohol concentration is between 1.0 w/v % and 7.0 w/v %, more preferable between 2.0 and 6.0 w/v %. Preferably amino acids include levorotary (L) forms of camitine, arginine, and betaine; however, other amino acids may be added. Preferred polymers include polyvinylpyrrolidone (PVP) with an average molecular weight between 2,000 and 3,000, or polyethylene glycol (PEG) with an average molecular weight between 3,000 and 5,000. It is also preferred to use a buffer in the composition to minimize pH changes in the solution before lyophilization or after reconstitution, if these are used. Most any physiological buffer may be used, but citrate, phosphate, succinate, and glutamate buffers or mixtures thereof are preferred. Preferably, the concentration is from 0.01 to 0.3 molar. Surfactants can also be added to the formulation.

Additionally, INGAP or polypeptide portions thereof can be chemically modified by covalent conjugation to a polymer to increase its circulating half-life, for example. Preferred polymers, and methods to attach them to peptides, are shown in U.S. Pat. Nos. 4,766,106, 4,179,337, 4,495,285, and 4,609,546. Preferred polymers an polyoxyethylated polyols and polyethylene glycol (PEG). PEG is soluble in water at room temperature and has the general formula: $R(O—CH_2—CH_2)_nO—R$ where R can be hydrogen, or a protective group such as an alkyl or alkanol group. Preferably, the protective group has between 1 and 8 carbons, more preferably it is methyl. The symbol n is a positive integer, preferably between 1 and 1,000, more preferably between 2 and 500. The PEG has a preferred average molecular weight between 1000 and 40,000, more preferably between 2000 and 20,000, most preferably between 3,000 and 12,000. Preferably, PEG has at least one hydroxy group, more preferably it is a terminal hydroxy group. It is this hydroxy group which is preferably activated to react with a free amino group on the inhibitor.

After the liquid pharmaceutical composition is prepared, it is preferably lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is preferably administered to subjects using those methods that are known to those skilled in the art.

The following examples are not intended to limit the scope of the invention, but merely to exemplify that which is taught above.

EXAMPLES

Example 1

This example describes the cloning and isolation of a cDNA encoding a novel, developmentally regulated, pancreatic protein.

We hypothesized that a unique locally produced factor(s) is responsible for islet cell regeneration. Using the recently developed mRNA differential display technique (5,6) to compare genes differentially expressed in cellophane wrapped (CW) versus control pancreata (CP) allowed us to identify a cDNA clone (RD19-2) which was uniquely expressed in cellophane wrapped pancreas.

A cDNA library was constructed from mRNA isolated from cellophane wrapped hamster pancreas using oligo d(T) primed synthesis, and ligation into pcDNA3 vector (Invitrogen). The number of primary recombinants in the library was $1.2\times10^4$ with an average size of 1.1 kb. The cDNA library was screened for clones of interest using high density colony plating techniques. Colonies were lifted onto nylon membranes (Schleicher & Schnell) and further digested with proteinase K (50(g/ml). Treated membranes were baked at 80° C. for 1 hour and hybridized at 50° C. for 16–18 hours with $1–5\times10^6$ cpm/ml of [($^{32}$P]-dCTP(Dupont-NewEngland Nuclear) radiolabeled RD19-2 probe. Colonies with a positive hybridization signal were isolated, compared for size with Northern mRNA transcript, and sequenced to confirm identity with the RD19-2 sequence.

Example 2

This example compares the sequence of INGAP to other proteins with which it shares homology.

The nucleotide sequence of the hamster INGAP clone with the longest cDNA insert was determined. As shown in FIGS. 1A and 1B the hamster cDNA comprises 747 nucleotides (nt), exclusive of the poly(A) tail and contains a major open reading frame encoding a 175 amino acid protein. The open reading frame is followed by a 3'-untranslated region of 206 nt. A typical polyadenylation signal is present 11 Nt upstream of the poly(A) tail. The predicted INGAP protein shows structural homology to both the PAP/HIP family of genes which is associated with pancreatitis or liver adenocarcinoma (7-11) and the Reg/PSP/lithostatine family of genes (13,15) which has been shown to stimulate pancreatic beta-cell growth (14) and might play a role in pancreatic islet regeneration. Comparison of the nucleotide sequence and their deduced amino acids between hamster INGAP and rat PAP-I shows a high degree of homology in the coding region (60 and 58% in nucleotide and amino acid sequences, respectively). The predicted amino acid sequence of the hamster INGAP reveals 45% identity to PAP II and 50% to PAP III both of which have been associated with acute pancreatitis, and 54% to HIP which was found in a hepatocellular carcinoma. INGAP also shows 40% identity to the rat Reg/PSP/lithostatine protein (FIG. 2). Reg is thought to be identical to the pancreatic stone protein (PSP) (15,16) or pancreatic thread protein (PM (17). The N-terminus of the predicted sequence of INGAP protein is highly hydrophobic which makes it a good candidate for being the signal peptide which would allow the protein to be secreted. Similar to PAP/HIP but different from the Reg/PSP/lithostatine proteins a potential N-glycosylation site is situated at position 135 of the INGAP sequence. Unique to INGAP is another potential N-glycosylation site situated at position 115. INGAP also shows a high degree of homology (12/18) (FIG. 2) with a consensus motif in members of the calcium-dependent (C-type) animal lectin as determined by Drickamer including four perfectly conserved cysteines which form two disulfide bonds (12). Two extra cysteines found at the amino-terminus of INGAP (FIG. 2) are also present in Reg/PSP and PAP/HIP. However, it is not clear what The biological significance might be.

Example 3

This example demonstrates the temporal expression pattern of INGAP upon cellophane-wrapping.

In order to determine the temporal expression of the INGAP gene, total RNA extracted from CP and CW pancreas was probed with the hamster INGAP cDNA clone in Northern blot analysis. A strong single transcript of 900 bp was detected (FIGS. 3A, 3B and 3C) 1 and 2 days after cellophane wrapping which disappeared by 6 through 42 days and was absent from CP. INGAP mRNA is associated with CW induced pancreatic islet neogenesis, since it is present only after CW. It is not likely that the increased expression of INGAP is associated with acute pancreatitis as is the case with the PAP family of genes. During the acute phase of pancreatitis the concentrations of most mRNAs encoding pancreatic enzymes including amylase are decreased significantly (16,18). In contrast, in the CW model of islet neogenesis in which high expression of INGAP has been detected, amylase gene expression was simultaneously increased above normal (FIGS. 3A, 3B and 3C) rather than decreased, suggesting that INGAP expressions not associated with pancreatitis but rather with islet neogenesis. The cause of increased amylase gene expression 1 and 2 days after CW is as yet unclear, and more studies need to be done to elucidate this issue. It is unlikely though, that the increase is associated with exocrine cell regeneration which occurs at a later time after CW (19). Thus, INGAP protein plays a role in stimulation of islet neogenesis, in particular, in beta cell regeneration from ductal cells.

References

1. Rosenberg, L, Brown, R. A. and Duguid, W. P. (1982). Surg. Forum 33, 227–230.
2. Rosenberg, L., Brown, R. A. and Duguid, W. P (1983). J. Surg, Res. 35, 63–72.
3. Rosenberg, L., Duguid, W. F. and Vinik, A. I (1987). Dig. Dis. Sci. 32, 1185.
4. Clas, D., Rosenberg, L. and Duguid, W. P. (1989). Pancreas 4, 613 (Abstract).
5. Liang, P and Pardee, B. A. (1992). Science 257,967–971.
6. Liang, P, Averboutkh, L. and Pardee, B. A. (1993). Nucleic Acid Res. 21, 3269–3275.
7. Iovanna, J., Orelle, B., Keim, V. and Dagorn, J. C. (1991). J. Biol. Chem. 266, 24664–24669.
8. Frigerio, J. M, Dusetti, N., Keim, V. Dagorn, J. C. and Iovanna, J. (1993). Biochemistry 32, 9236–9241.
9. Frigerio, J. M., Dusetti, N., Garrido, P, Dagorn, J. C. and Iovanna, J. (1993). Biochim. Biophys. Actsa 1216, 329–331.
10. Orelle, B, Keim, V, Masciotra, L, Dagorn, J. C. and Iovanna, J. (1992). J. Clin. Invest. 90,2284–2291.

11. Lasserre, C., Christa, L, Simon, M. T, Vernier, P. and Brechot, C. (1992). Cancer Res. 52, 5089–5095.
12. Drickamer, K. (1988), J. Biol. Chem. 263, 9557–9560.
13. Terazono, K., Yamamoto, H., Takasawa, S., Shiga, K., Yonemura, Y., Tochino, Y. and Okamoto, H. (1988). J. Biol. Chem. 263, 2111–2114.
14. Watanabe, T., Yutaka, Y., Yonekura, H., Suzuki, Y., Miyashita, H., Sugiyama, K., Morizumi, S., Unno, M., Tanaka, O., Kondo, H., Bone, A. J., Takasawa, S. and Okamoto, H. (1994). Proc. Natl. Acad. Sci. USA 91, 3589–3592.
15. Rouquier, S., Giorgi, D., Iovanna, J. and Dagorn, J. C. (1989). Biochem. J. 264, 621–624.
16. Rouquier, S., Verdier, J., Iovanna, J., Dagorn, J. C. and Giorgi, D. (1991) J. Biol. Chem. 266, 786–791.
17. Gross, J., Carlson, R. L, Brauer, A. W. Margolies, M. N., Warshaw, A. L. and Wands, J. R. (1985), J. Clin. Invest. 76,2115–2126.
18. Iovanna, J., Keim,V., Michael, R. and Dagorn, J. C. (1991). Am. J. Physiol. 261, G485–G489.
19. Rosenberg, L., and Vinik, A. I. (1989), J. Lab. Clin. Med. 114, 75–83.

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
(A) LENGTH: 747 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (vi) ORIGINAL SOURCE:
(A) ORGANISM: Cricetulus (ix) FEATURE:
(A) NAME/KEY: CDS
(B) LOCATION: 20..541

(xi) SEQUENCE DESCRIPTION: SEQ ID NO: 1:

```
CTGCAAGACA GGTACCATG ATG CTT CCC ATG ACC CTC TGT AGG ATG TCT TGG      52
                     Met Leu Pro Met Thr Leu Cys Arg Met Ser Trp
                       1               5                  10

ATG CTG CTT TCC TGC CTG ATG TTC CTT TCT TGG GTG GAA GGT GAA GAA      100
Met Leu Leu Ser Cys Leu Met Phe Leu Ser Trp Val Glu Gly Glu Glu
            15                  20                  25

TCT CAA AAG AAA CTG CCT TCT TCA CGT ATA ACC TGT CCT CAA GGC TCT      148
Ser Gln Lys Lys Leu Pro Ser Ser Arg Ile Thr Cys Pro Gln Gly Ser
        30                  35                  40

GTA GCC TAT GGG TCC TAT TGC TAT TCA CTG ATT TTG ATA CCA CAG ACC      196
Val Ala Tyr Gly Ser Tyr Cys Tyr Ser Leu Ile Leu Ile Pro Gln Thr
    45                  50                  55

TGG TCT AAT GCA GAA CTA TCC TGC CAG ATG CAT TTC TCA GGA CAC CTG      244
Trp Ser Asn Ala Glu Leu Ser Cys Gln Met His Phe Ser Gly His Leu
60                  65                  70                  75

GCA TTT CTT CTC AGT ACT GGT GAA ATT ACC TTC GTG TCC TCC CTT GTG      292
Ala Phe Leu Leu Ser Thr Gly Glu Ile Thr Phe Val Ser Ser Leu Val
                80                  85                  90

AAG AAC AGT TTG ACG GCC TAC CAG TAC ATC TGG ATT GGA CTC CAT GAT      340
Lys Asn Ser Leu Thr Ala Tyr Gln Tyr Ile Trp Ile Gly Leu His Asp
            95                  100                 105

CCC TCA CAT GGT ACA CTA CCC AAC GGA AGT GGA TGG AAG TGG AGC AGT      388
Pro Ser His Gly Thr Leu Pro Asn Gly Ser Gly Trp Lys Trp Ser Ser
        110                 115                 120

TCC AAT GTG CTG ACC TTC TAT AAC TGG GAG AGG AAC CCC TCT ATT GCT      436
```

-continued

```
Ser Asn Val Leu Thr Phe Tyr Asn Trp Glu Arg Asn Pro Ser Ile Ala
    125                 130                 135

GCT GAC CGT GGT TAT TGT GCA GTT TTG TCT CAG AAA TCA GGT TTT CAG      484
Ala Asp Arg Gly Tyr Cys Ala Val Leu Ser Gln Lys Ser Gly Phe Gln
140                 145                 150                 155

AAG TGG AGA GAT TTT AAT TGT GAA AAT GAG CTT CCC TAT ATC TGC AAA      532
Lys Trp Arg Asp Phe Asn Cys Glu Asn Glu Leu Pro Tyr Ile Cys Lys
                160                 165                 170

TTC AAG GTC TAGGGCAGTT CTAATTTCAA CAGAGAGCAA GCTCTGCCTA CACACCCACA   591
Phe Lys Val

CCAATTCCCT TATATCATCT CTGCTGTTTT TCCTTGAAAT TATTATGAAG CTCACATGGA    651

CAAGGAAGCA AGTATGAGGA TTCACTCAGG ATATCAGTAT ATTCTGTGGT GGCTGTAACC    711

TAAAGGCTCA GAGAACAAAA ATAAAATGTC ATCAAC                              747
```

(2) INFORMATION FOR SEQ ID NO: 2:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 2:

```
Met Leu Pro Met Thr Leu Cys Arg Met Ser Trp Met Leu Leu Ser Cys
  1               5                  10                  15

Leu Met Phe Leu Ser Trp Val Glu Gly Glu Glu Ser Gln Lys Lys Leu
             20                  25                  30

Pro Ser Ser Arg Ile Thr Cys Pro Gln Gly Ser Val Ala Tyr Gly Ser
         35                  40                  45

Tyr Cys Tyr Ser Leu Ile Leu Ile Pro Gln Thr Trp Ser Asn Ala Glu
     50                  55                  60

Leu Ser Cys Gln Met His Phe Ser Gly His Leu Ala Phe Leu Leu Ser
 65                  70                  75                  80

Thr Gly Glu Ile Thr Phe Val Ser Ser Leu Val Lys Asn Ser Leu Thr
                 85                  90                  95

Ala Tyr Gln Tyr Ile Trp Ile Gly Leu His Asp Pro Ser His Gly Thr
            100                 105                 110

Leu Pro Asn Gly Ser Gly Trp Lys Trp Ser Ser Ser Asn Val Leu Thr
        115                 120                 125

Phe Tyr Asn Trp Glu Arg Asn Pro Ser Ile Ala Ala Asp Arg Gly Tyr
    130                 135                 140

Cys Ala Val Leu Ser Gln Lys Ser Gly Phe Gln Lys Trp Arg Asp Phe
145                 150                 155                 160

Asn Cys Glu Asn Glu Leu Pro Tyr Ile Cys Lys Phe Lys Val
                165                 170
```

(2) INFORMATION FOR SEQ ID NO: 3:

(i) SEQUENCE CHARACTERISTICS:
(A) LENGTH: 175 amino acids
(B) TYPE: amino acid
(D) TOPOLOGY: linear (ii) MOLECULE TYPE: protein (iv) ANTI-SENSE: NO (vi) ORIGINAL SOURCE:
(A) ORGANISM: Rattus rattus -continued (xi) SEQUENCE DESCRIPTION: SEQ ID NO: 3:

```
Met Leu His Arg Leu Ala Phe Pro Val Met Ser Trp Met Leu Leu Ser
1               5                   10                  15

Cys Leu Met Leu Leu Ser Gln Val Gln Gly Glu Asp Ser Pro Lys Lys
            20                  25                  30

Ile Pro Ser Ala Arg Ile Ser Cys Pro Lys Gly Ser Gln Ala Tyr Gly
        35                  40                  45

Ser Tyr Cys Tyr Ala Leu Phe Gln Ile Pro Gln Thr Trp Phe Asp Ala
    50                  55                  60

Glu Leu Ala Cys Gln Lys Arg Pro Glu Gly His Leu Val Ser Val Leu
65                  70                  75                  80

Asn Val Ala Glu Ala Ser Phe Leu Ala Ser Met Val Lys Asn Thr Gly
                85                  90                  95

Asn Ser Tyr Gln Tyr Ile Trp Ile Gly Leu His Asp Pro Thr Leu Gly
            100                 105                 110

Gly Glu Pro Asn Gly Gly Gly Trp Glu Trp Ser Asn Asn Asp Ile Met
        115                 120                 125

Asn Tyr Val Asn Trp Glu Arg Asn Pro Ser Thr Ala Leu Asp Arg Gly
    130                 135                 140

Phe Cys Gly Ser Leu Ser Arg Ser Ser Gly Phe Leu Arg Trp Arg Asp
145                 150                 155                 160

Thr Thr Cys Glu Val Lys Leu Pro Tyr Val Cys Lys Phe Thr Gly
                165                 170                 175
```

(2) INFORMATION FOR SEQ ID NO: 4:

(i) SEQUENCE CHARACTERISTICS:
(A) LENGTH: 175 amino acids
(B) TYPE: amino acid
(D) TOPOLOGY: linear (ii) MOLECULE TYPE: protein (vi) ORIGINAL SOURCE:
(A) ORGANISM: Homo sapiens (xi) SEQUENCE DESCRIPTION: SEQ ID NO: 4:

```
Met Leu Pro Pro Met Ala Leu Pro Ser Val Ser Trp Met Leu Leu Ser
1               5                   10                  15

Cys Leu Met Leu Leu Ser Gln Val Gln Gly Glu Glu Pro Gln Arg Glu
            20                  25                  30

Leu Pro Ser Ala Arg Ile Arg Cys Pro Lys Gly Ser Lys Ala Tyr Gly
        35                  40                  45

Ser His Cys Tyr Ala Leu Phe Leu Ser Pro Lys Ser Trp Thr Asp Ala
    50                  55                  60

Asp Leu Ala Cys Gln Lys Arg Pro Ser Gly Asn Leu Val Ser Val Leu
65                  70                  75                  80

Ser Gly Ala Glu Gly Ser Phe Val Ser Ser Leu Val Lys Ser Ile Gly
                85                  90                  95

Asn Ser Tyr Ser Tyr Val Trp Ile Gly Leu His Asp Pro Thr Gln Gly
            100                 105                 110

Thr Glu Pro Asn Gly Glu Gly Trp Glu Trp Ser Ser Ser Asp Val Met
        115                 120                 125

Asn Tyr Phe Ala Trp Glu Arg Asn Pro Ser Thr Ile Ser Ser Pro Gly
    130                 135                 140

His Cys Ala Ser Leu Ser Arg Ser Thr Ala Phe Leu Arg Trp Lys Asp
```

-continued

```
145                 150                 155                 160

Tyr Asn Cys Asn Val Arg Leu Pro Tyr Val Cys Lys Phe Thr Asp
                165                 170                 175


(2) INFORMATION FOR SEQ ID NO: 5:

     (i) SEQUENCE CHARACTERISTICS:
          (A) LENGTH: 174 amino acids
          (B) TYPE: amino acid
          (D) TOPOLOGY: linear

    (ii) MOLECULE TYPE: protein

    (vi) ORIGINAL SOURCE:
          (A) ORGANISM: Rattus rattus

    (xi) SEQUENCE DESCRIPTION: SEQ ID NO: 5:

Met Leu Pro Arg Val Ala Leu Thr Thr Met Ser Trp Met Leu Leu Ser
1               5                   10                  15

Ser Leu Met Leu Leu Ser Gln Val Gln Gly Glu Asp Ala Lys Glu Asp
            20                  25                  30

Val Pro Thr Ser Arg Ile Ser Cys Pro Lys Gly Ser Arg Ala Tyr Gly
        35                  40                  45

Ser Tyr Cys Tyr Ala Leu Phe Ser Val Ser Lys Ser Trp Phe Asp Ala
    50                  55                  60

Asp Leu Ala Cys Gln Lys Arg Pro Ser Gly His Leu Val Ser Val Leu
65                  70                  75                  80

Ser Gly Ser Glu Ala Ser Phe Val Ser Ser Leu Ile Lys Ser Ser Gly
                85                  90                  95

Asn Ser Gly Gln Asn Val Trp Ile Gly Leu His Asp Pro Thr Leu Gly
            100                 105                 110

Gln Glu Pro Asn Arg Gly Gly Trp Glu Trp Ser Asn Ala Asp Val Met
        115                 120                 125

Asn Tyr Phe Asn Trp Glu Thr Asn Pro Ser Ser Val Ser Gly Ser His
    130                 135                 140

Cys Gly Thr Leu Thr Arg Ala Ser Gly Phe Leu Arg Trp Arg Glu Asn
145                 150                 155                 160

Asn Cys Ile Ser Glu Leu Pro Tyr Val Cys Lys Phe Lys Ala
                165                 170


(2) INFORMATION FOR SEQ ID NO: 6:

     (i) SEQUENCE CHARACTERISTICS:
          (A) LENGTH: 174 amino acids
          (B) TYPE: amino acid
          (D) TOPOLOGY: linear

    (ii) MOLECULE TYPE: protein

    (vi) ORIGINAL SOURCE:
          (A) ORGANISM: Rattus rattus

    (xi) SEQUENCE DESCRIPTION: SEQ ID NO: 6:

Met Leu Pro Arg Leu Ser Phe Asn Asn Val Ser Trp Thr Leu Leu Tyr
1               5                   10                  15

Tyr Leu Phe Ile Phe Gln Val Arg Gly Glu Asp Ser Gln Lys Ala Val
            20                  25                  30

Pro Ser Thr Arg Thr Ser Cys Pro Met Gly Ser Lys Ala Tyr Arg Ser
        35                  40                  45

Tyr Cys Tyr Thr Leu Val Thr Thr Leu Lys Ser Trp Phe Gln Ala Asp
    50                  55                  60
```

-continued

```
Leu Ala Cys Gln Lys Arg Pro Ser Gly His Leu Val Ser Ile Leu Ser
65                  70                  75                  80

Gly Gly Glu Ala Ser Phe Val Ser Ser Leu Val Thr Gly Arg Val Asn
                85                  90                  95

Asn Asn Gln Asp Ile Trp Ile Trp Leu His Asp Pro Thr Met Gly Gln
            100                 105                 110

Gln Pro Asn Gly Gly Gly Trp Glu Trp Ser Asn Ser Asp Val Leu Asn
        115                 120                 125

Tyr Leu Asn Trp Asp Gly Asp Pro Ser Ser Thr Val Asn Arg Gly Asn
    130                 135                 140

Cys Gly Ser Leu Thr Ala Thr Ser Glu Phe Leu Lys Trp Gly Asp His
145                 150                 155                 160

His Cys Asp Val Glu Leu Pro Phe Val Cys Lys Phe Lys Gln
                165                 170


(2) INFORMATION FOR SEQ ID NO: 7:

     (i) SEQUENCE CHARACTERISTICS:
          (A) LENGTH: 165 amino acids
          (B) TYPE: amino acid
          (D) TOPOLOGY: linear

    (ii) MOLECULE TYPE: protein

    (vi) ORIGINAL SOURCE:
          (A) ORGANISM: Rattus rattus

    (xi) SEQUENCE DESCRIPTION: SEQ ID NO: 7:

Met Thr Arg Asn Lys Tyr Phe Ile Leu Leu Ser Cys Leu Met Val Leu
1               5                   10                  15

Ser Pro Ser Gln Gly Gln Glu Ala Glu Glu Asp Leu Pro Ser Ala Arg
            20                  25                  30

Ile Thr Cys Pro Glu Gly Ser Asn Ala Tyr Ser Ser Tyr Cys Tyr Tyr
        35                  40                  45

Phe Met Glu Asp His Leu Ser Trp Ala Glu Ala Asp Leu Phe Cys Gln
    50                  55                  60

Asn Met Asn Ser Gly Tyr Leu Val Ser Val Leu Ser Gln Ala Glu Gly
65                  70                  75                  80

Asn Phe Leu Ala Ser Leu Ile Lys Glu Ser Gly Thr Thr Ala Ala Asn
                85                  90                  95

Val Trp Ile Gly Leu His Asp Pro Lys Asn Asn Arg Arg Trp His Trp
            100                 105                 110

Ser Ser Gly Ser Leu Phe Leu Tyr Lys Ser Trp Asp Thr Gly Tyr Pro
        115                 120                 125

Asn Asn Ser Asn Arg Gly Tyr Cys Val Ser Val Thr Ser Asn Ser Gly
    130                 135                 140

Tyr Lys Lys Trp Arg Asp Asn Ser Cys Asp Ala Gln Leu Ser Phe Val
145                 150                 155                 160

Cys Lys Phe Lys Ala
                165
```

We claim:

1. A preparation of a naturally occurring mammalian islet neogenesis associated protein (INGAP protein) substantially free of other mammalian proteins, *wherein the INGAP protein has the amino acid sequence shown in SEQ ID NO: 2*.

[2. The preparation of claim 1 wherein the INGAP protein has the amino acid sequence shown in SEQ ID NO: 2.]

3. A preparation of a polypeptide which comprises a sequence of at least 15 consecutive amino acids of a naturally occurring mammalian islet neogenesis associated protein (INGAP protein), wherein said polypeptide has immunogenic activity *and wherein said sequence is a portion of*

*INGAP protein, wherein the INGAP protein has the amino acid sequence shown in SEQ ID NO: 2.*

4. [The preparation of claim 3 wherein said] *A* polypeptide *which* is a fusion of [said] *(1) a first* sequence *of at least 15 consecutive amino acids of a naturally occurring mammalian islet neogenesis associated protein (INGAP protein), wherein the INGAP protein has the amino acid sequence shown in SEQ ID NO: 2, wherein said first sequence has immunogenic activity* to *(2)* a second [polypeptide] *sequence* derived from a second protein.

5. The preparation of claim 3 wherein said polypeptide is conjugated to a second polypeptide.

6. The preparation of claim 3 wherein said polypeptide is conjugated to a solid support.

7. The preparation of claim 3 wherein said polypeptide [has a biological activity of said mammalian INGAP protein] *is capable of stimulating beta cell regeneration in pancreatic ductal cells.*

8. The preparation of claim [7] *3* wherein [said biological activity is] *the polypeptide has* the ability to stimulate pancreatic duct cells to grow and proliferate.

9. The preparation of claim 3 wherein said polypeptide comprises amino acids #103 to #122 of the mammalian INGAP protein as shown in SEQ ID NO:2.

10. The preparation of claim 3 wherein said polypeptide comprises at least 130 consecutive amino acids of said mammalian INGAP protein as defined by SEQ ID NO:2.

11. A preparation of an islet [eogenesis] *neogenesis* associated protein (INGAP protein) of a mammal *according to claim 1,* [substantially purified from other proteins of the mammal] wherein said INGAP protein is [inducible upon] *made by the process of inducing production of said protein by* cellophane-wrapping of pancreas of the mammal.

12. A pharmaceutical composition for treatment of pancreatic insufficiency, comprising:

a naturally occurring mammalian islet neogenesis associated protein (INGAP protein) in a pharmaceutically acceptable diluent or carrier, *wherein the INGAP protein has the amino acid sequence shown in SEQ ID NO: 2.*

[13. The pharmaceutical composition of claim 12 wherein the INGAP protein has the amino acid sequence shown in SEQ ID NO: 2.]

14. A pharmaceutical composition comprising:

a preparation of a polypeptide which comprises a sequence of at least 15 consecutive amino acids of a naturally occurring mammalian islet neogenesis associated protein (INGAP protein) and a pharmaceutically acceptable diluent or carrier, wherein said polypeptide is capable of stimulating β cell regeneration of pancreatic ductal cells, *wherein the INGAP protein has the amino acid sequence shown in SEQ ID NO: 2, and wherein said sequence is a portion of said INGAP protein.*

15. [The] *A* pharmaceutical composition [of claim 14 wherein said polypeptide is a fusion of said sequence to a second polypeptide derived from a second protein] *comprising:*

*a preparation of a fusion polypeptide which is a fusion of (1) first sequence of at least 15 consecutive amino acids of a naturally occurring mammalian islet neogenesis associated protein (INGAP protein), wherein the first sequence is capable of stimulating β cell regeneration of pancreatic ductal cells, to (2) a second sequence derived from a second protein; and*

*a pharmaceutically acceptable diluent or carrier,*

*wherein said fusion polypeptide is capable of stimulating β cell regeneration of pancreatic ductal cells, and wherein the INGAP protein has the amino acid sequence shown in SEQ ID NO: 2.*

16. The pharmaceutical composition of claim 14 wherein said polypeptide is conjugated to a second polypeptide.

[17. The pharmaceutical composition of claim 14 wherein said polypeptide has a biological activity of said mammalian INGAP protein.]

[18. The pharmaceutical composition of claim 17 wherein said biological activity is the ability to stimulate pancreatic duct cells to grow and proliferate.]

19. The pharmaceutical composition of claim 14 wherein said polypeptide comprises amino acids #103 to #122 of the mammalian INGAP protein as shown in SEQ ID NO:2.

20. The pharmaceutical composition of claim 14 wherein said polypeptide comprises at least 130 consecutive amino acids of said mammalian INGAP protein as defined by SEQ ID NO:2.

21. The preparation of claim 1 which is free of other mammalian proteins.

22. The preparation of claim 11 which is free from other proteins of the mammal.

23. The preparation of claim 11 wherein the INGAP protein has 174 amino acids.

24. The preparation of claim 11 wherein the INGAP protein is purified utilizing antibodies which immunoreact with INGAP.

*25. The preparation of claim 1 wherein the INGAP protein is made by a process of expression in a host cell which comprises a vector which comprises a nucleotide sequence which encodes the INGAP protein.*

*26. The preparation of claim 3 wherein said polypeptide is made by a process of expression in a host cell which comprises a vector which comprises a nucleotide sequence which encodes the polypeptide.*

*27. The pharmaceutical composition of claim 12 wherein said INGAP protein is substantially free of other mammalian proteins.*

*28. The pharmaceutical composition of claim 14 wherein said polypeptide is substantially free of other mammalian protein.*

*29. A preparation of a polypeptide which comprises a sequence of at least 15 consecutive amino acids shown in SEQ ID NO: 2, wherein said sequence is a portion of islet neogenesis associated protein (INGAP protein) capable of stimulating β cell regeneration of pancreatic ductal cells.*

*30. The preparation of claim 29 wherein the polypeptide comprises a sequence of at least 15 consecutive amino acids selected from amino acids #103 to #122 as shown in SEQ ID NO: 2.*

*31. A pharmaceutical composition comprising a preparation of a polypeptide which comprises a sequence of at least 15 consecutive amino acids shown in SEQ ID NO: 2, wherein said sequence is capable of stimulating β cell regeneration in pancreatic ductal cells, wherein said sequence is a portion of islet neogenesis associated protein (INGAP protein).*

*32. The pharmaceutical composition of claim 31 wherein the polypeptide comprises a sequence of at least 15 consecutive amino acids selected from amino acids #103 to #122 as shown in SEQ ID NO: 2.*

*33. A preparation of a polypeptide which consists of a portion of islet neogenesis associated protein (INGAP protein) of at least 15 consecutive amino acids shown in SEQ ID NO: 2; wherein said polypeptide is capable of stimulating β cell regeneration of pancreatic ductal cells.*

*34. The preparation of claim 33 wherein the polypeptide consists of a portion of islet neogenesis associated protein (INGAP protein) of at least 15 consecutive amino acids selected from amino acids #103 to #122 as shown in SEQ ID NO: 2.*

*35. A pharmaceutical composition comprising a polypeptide which consists of a portion of islet neogenesis associated protein (INGAP protein) of at least 15 consecutive amino acids shown in SEQ ID NO: 2, wherein said polypeptide is capable of stimulating β cell regeneration in pancreatic ductal cells.*

*36. The pharmaceutical composition of claim 35 wherein the polypeptide consists of a portion of islet neogenesis associated protein (INGAP protein) of at least 15 consecutive amino acids selected from amino acids #103 to #122 as shown in SEQ ID NO: 2.*

* * * * *